(12) United States Patent
Learmonth et al.

(10) Patent No.: US 7,834,177 B2
(45) Date of Patent: Nov. 16, 2010

(54) METHOD FOR PREPARATION OF 10,11-DIHYDRO-10-HYDROXY-5H-DIBENZ/B,F/AZEPINE-5-CARBOXAMIDE

(75) Inventors: David Alexander Learmonth, Alfena (PT); Günter Weingärtner, Dottikon (CH); Matthias Kraemer, Mellingen (CH)

(73) Assignee: Bial - Portela & CA, S.A., S. Mamede Do Coronado (PT)

( * ) Notice: Subject to any disclaimer, the term of this patent is extended or adjusted under 35 U.S.C. 154(b) by 671 days.

(21) Appl. No.: 11/813,938

(22) PCT Filed: Jan. 13, 2006

(86) PCT No.: PCT/PT2006/000002

§ 371 (c)(1),
(2), (4) Date: Oct. 31, 2007

(87) PCT Pub. No.: WO2006/075925

PCT Pub. Date: Jul. 20, 2006

(65) Prior Publication Data

US 2008/0139807 A1  Jun. 12, 2008

(30) Foreign Application Priority Data

Jan. 14, 2005 (GB) .................................. 0500815.6

(51) Int. Cl.
C07D 223/22 (2006.01)
C07D 491/04 (2006.01)
(52) U.S. Cl. ..................................... 540/589
(58) Field of Classification Search .................. 540/589
See application file for complete search history.

(56) References Cited

U.S. PATENT DOCUMENTS

| 3,842,091 | A  | 10/1974 | Kawashima et al. |
| 5,753,646 | A  | 5/1998  | Benés et al. |
| 5,808,058 | A  | 9/1998  | Milanese |
| 7,241,886 | B2 | 7/2007  | Learmonth |

FOREIGN PATENT DOCUMENTS

| CH | 642950 | | 5/1984 |
| DE | 2246842 | | 4/1973 |
| EP | 0751129 | A1 | 1/1997 |
| GB | 1402325 | | 8/1975 |
| HU | 63390 | A2 | 8/1993 |
| NL | 7902811 | | 10/1979 |
| WO | 9621649 | A1 | 7/1996 |
| WO | 9738978 | A1 | 10/1997 |
| WO | 0055138 | A1 | 9/2000 |
| WO | 02096881 | A1 | 12/2002 |
| WO | 2006075925 | A2 | 7/2006 |
| WO | 2006075925 | A3 | 7/2006 |

OTHER PUBLICATIONS

Baker, K. M., et al., "10,11-Dihydro-10,11-dihydroxy-5H-dibenz[b,f]azepine-5-carboxamide, a metabolite of carbamazepine isolated from human and rat urine," XP-002209649, 1973, pp. 703-705, vol. 16, No. 6, Journal of Medicinal Chemistry.
Bellucci, Giuseppe, et al., "The metabolism of carbamazepine in humans: steric course of the enzymatic hydrolysis of the 10,11-epoxide," XP-002209650, Journal of Medicinal Chemistry, 1987, pp. 768-773, vol. 30, No. 5, American Chemical Society.
Benes, Jan, et al., "Anticonvulsant and sodium channel-blocking properties of novel 10,11-dihydro-5H-dibenz[b,f]azepine-5-carboxamide derivatives," XP-002206156, Journal of Medicinal Chemistry, 1999, pp. 2582-2587, vol. 42, No. 14, American Chemical Society.
Canali, L., et al., "Synthesis of resins with pendently-bound chiral manganese—salen complexes and use as heterogeneous asymmetric alkene epoxidation catalysts," Reactive & Functional Polymers, 1999, pp. 155-168, vol. 40, Elsevier Science B.V.
Chemical Abstracts Reference 120:75516, "Preparation of 10,11-epoxycarbamazepine and 10,11-dihydro-10-hydroxycarbamazepine by microbial epoxidation and hydroxylation" by Matthias Kittelmann, et al., 2008, 1 page, ACS on STN.
Chemical Abstracts Reference 125:86408, "Cobalt-mediated olefin epoxidation and oxidative DNA cleavage with potassium monopersulfate" by Wonwoo Nam, et al., 2008, 1 page, ACS on STN.
Chemical Abstracts Reference 128:140628, "Water-soluble iron porphyrin complex-catalyzed epoxidation of olefins with hydrogen peroxide and tert-butyl hydroperoxide in aqueous solution" by Sook Jung Yang, et al., 2008, 1 page, ACS on STN.
Corey, E. J., et al., "A new Cr(VI) reagent for the catalytic oxidation of secondary alcohols to ketones," Tetrahedron Letters, 1985, pp. 5855-5858, vol. 26, No. 48, Pergamon Press Ltd., Great Britain.
Foreign communication from a related counterpart application—International Search Report, PCT/GB02/02356, Oct. 25, 2002, 10 pages.
Foreign communication from a related counterpart application—International Search Report and Written Opinion, PCT/PT2006/000002, Jul. 6, 2006, 6 pages.
Grant, Susan M., et al., "Oxcarbazepine: a review of its pharmacology and therapeutic potential in epilepsy, trigeminal neuralgia and affective disorders," XP 002039768, Drugs, 1992, pp. 873-888, vol. 43, No. 6, Adis International Limited.
Hudlický, Miloš, "Oxidations in organic chemistry," ACS Monograph 186, 1990, pp. 10-13 plus 1 cover sheet and 1 publishing page, American Chemical Society, USA.
Kittelman, Matthias, et al., "Preparation of 10,11-epoxy-carbamazepine and 10,11-dihydro-10-hydroxy-carbamazepine by microbial epoxidation and hydroxylation," 1993, pp. 1589-1590, vol. 57, No. 9, Biosci. Biotech. Biochem.

(Continued)

*Primary Examiner*—Brenda L Coleman
(74) *Attorney, Agent, or Firm*—Conley Rose, P.C.; Rodney B. Carroll

(57) ABSTRACT

A process for the preparation of 10,11-dihydro-10-hydroxy-5H-dibenz/b,f/azepine-5-carboxamide (1) by ring opening of 11a,10b-dihydro-6H-dibenz/b,f/oxireno[d]azepine-6-carboxamide (5), characterised in that the ring opening is carried out under conditions of elevated pressure.

15 Claims, No Drawings

OTHER PUBLICATIONS

Murahashi, Shun-Ichi, et al., "Ruthenium-catalyzed oxidation of alcohols with peracids," XP-001093973, Jul. 1995, pp. 733-734, Synlett.

Nam, Wonwoo, et al., "Cobalt-mediated olefin epoxidation and oxidative DNA cleavage with potassium monopersulfate," 1996, pp. 414-416, vol. 17, No. 5, Bull. Korean Chem. Soc.

Oshima, Masato, et al., "Palladium-catalyzed selective hydrogenolysis of alkenyloxiranes with formic acid. Stereoselectivity and synthetic utility," XP-002209651, J. Am. Chem. Soc., 1989, pp. 6280-6287, vol. 111, No. 16, American Chemical Society.

Schütz, H., et al., "The metabolism of 14C-oxcarbazepine in man," 1986, pp. 769-778, vol. 16, No. 8, Xenobiotica.

Senanayake, Chris H., et al., "The role of 4-(3-Phenylpropyl)pyridine N-oxide (P3NO) in the manganese-salen-catalyzed asymmetric epoxidation of indene," Tetrahedron Letters, 1996, pp. 3271-3274, vol. 37, No. 19, Elsevier Science Ltd, Pergamon, Great Britian.

Yang, Sook Jung, et al., "Water-soluble iron porphyrin complex-catalyzed epoxidation of olefins with hydrogen peroxide and tert-butyl hydroperoxide in aqueous solution," Inorganic Chemistry, 1998, pp. 606-607, vol. 37, No. 4, American Chemical Society.

Foreign communication from the priority application—International Preliminary Report on Patentability, PCT/PT2006/000002, Jul. 17, 2007, 5 pages.

METHOD FOR PREPARATION OF 10,11-DIHYDRO-10-HYDROXY-5H-DIBENZ/B,F/ AZEPINE-5-CARBOXAMIDE

This application is a national stage entry under 35 U.S.C. §371 of PCT/PT06/00002, filed Jan. 13, 2006.

The present invention relates to a process for the preparation of 10,11-dihydro-10-hydroxy-5H-dibenz/b,f/azepine-5-carboxamide (1).

The invention also relates to the use of the compound (1) as a starting material for the manufacture of the compound 10,11-dihydro-10-oxo-5H-dibenz/b,f/azepine-5-carboxamide (2). Compound (2), known as oxcarbazepine, possesses valuable properties for the treatment of epilepsy and is claimed to be a better-tolerated drug than carbamazepine (compound 3, where R=NH$_2$), a structurally-related anticonvulsant drug (Grant, S. M. et al., Drugs, 43, 873-888 (1992)). Compound (1) is also a known compound with anticonvulsant activity and is in fact the major metabolite of (2) (Schutz, H. et al., Xenobiotica, 16, 769-778 (1986)).

In addition to their anticonvulsant activities, compounds (1) and (2) serve also as useful intermediates for the preparation of (S)-(-)-10-acetoxy-10,11-dihydro-5H-dibenz/b,f/azepine-5-carboxamide (4), a more recently disclosed anticonvulsant (Benes, J. et al., J. Med. Chem., 42, 2582-2587 (1999), U.S. Pat. No. 5,753,646 & EP0751129B). Therefore, a short, economic, high-yielding and environmentally acceptable process for large-scale preparation of both would be desirable, starting preferably from a common, readily available precursor.

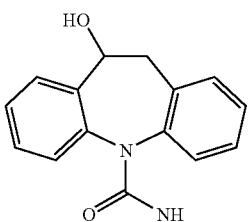
(1)

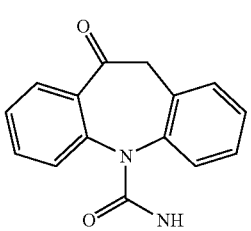
(2)

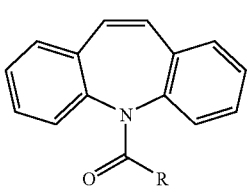
(3)

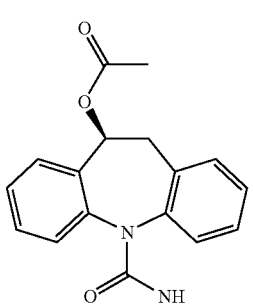
(4)

Previously described syntheses of the hydroxy compound (I) have entailed firstly epoxidation of either carbamazepine (i.e. compound 3, where R=NH$_2$) or the chloro-analogue (i.e. compound 3, where R=Cl) using m-chloroperoxybenzoic acid, thus affording the epoxides (i.e. compound 5, where R is NH$_2$ or Cl) in only moderate yield (~60%) (Bellucci, G. et al., J. Med. Chem., 30, 768-773 (1987)). Amination with ammonia then gives rise to compound (5).

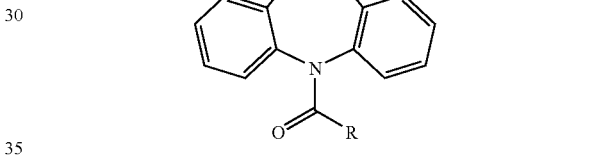
(5)

The major drawbacks, however, are that m-chloroperoxybenzoic acid is potentially explosive and so strict safety measures must accompany its use. Additionally, for this epoxidation a considerable excess of the expensive reagent is necessary. Therefore it is not amenable to large-scale syntheses and indeed many commercial sources have now ceased to produce this hazardous reagent. Other reports of epoxidation of compound (3) include microbial epoxidation (Kittelmann, M. et al., Biosci. Biotechnol. Biochem., 57(9), 1589-1590 (1993); Chem. Abstr. 120:75516), iron porphyrin/peroxide catalysed epoxidation (Yang, S. J. et al., Inorg. Chem., 37(4), 606-607 (1998); (Chem. Abstr. 128:140628), and cobalt-mediated epoxidation with persulfate (Nam, W. et al., Bull. Korean Chem. Soc., 17(5), 414-416 (1996); (Chem. Abstr. 125:86408). These methods are nonetheless unsuitable for large-scale production.

Many of the problems associated with the manufacture of the compound (5) were overcome in our WO0296881, the contents of which are hereby incorporated by reference.

The epoxide (5) is a versatile intermediate. Rearrangement Using halides of lithium and magnesium has given direct access to oxcarbazepine (2) (NL 7902811 & HU 63390). These reagents are, however, moisture-sensitive, are expensive from commercial sources or require preparation in sit-L, and yields of (2) are often low to moderate. Alternatively, the epoxide (5) has been converted to the alcohol (1) by catalytic hydrogenation using palladium (Baker, K. M. et al., J. Med. Chem., 16(6), 703-705 (1973)). However the catalyst loadings were very high and the overall yield of the alcohol was only moderate.

Oxcarbazepine has been manufactured by a number of processes using different starting materials (WO9621649 & WO0055138). Its preparation by direct oxidation of the alcohol (1) was first described in WO02/96881.

WO02/96881 also discloses a process for making the compound (1) from the compound (5), by a ring opening reaction. In WO02/96881, the ring-opening of the epoxide (5) is carried out by either catalytic transfer hydrogenation in the presence of a hydrogen donor and metal catalyst, or alternatively by catalytic hydrogenation with gaseous hydrogen in the presence of a metal catalyst.

The reaction described in WO02/96881 works well on a laboratory scale, but we have found that when it is scaled up to an industrial process there is a negative impact on the reaction yield and product purity. It is therefore an object of the present invention to provide a process which has good reaction yield and product purity.

We have now unexpectedly found that the reaction yield and product purity of the compound (1) can be improved by carrying out the ring opening of the epoxide (5) under conditions of elevated pressure, and preferably under conditions of elevated temperature. It is unexpected that the use of an elevated pressure would have this effect, since a person skilled in the art would predict that the use of an elevated pressure would result in an over reduction of the compound (1) to a completely saturated system. The use of elevated pressure, also unexpectedly, makes it possible to reduce the amount of solvent which is required in the reaction.

Thus, according to one aspect of the present invention there is provided a method for the preparation of 10,11-dihydro-10-hydroxy-5H-dibenz/b,f/azepine-5-carboxamide (1) by ring opening of the 11a,10b-dihydro-6H-dibenz/b,f/oxireno[d]azepine-6-carboxamide (5), wherein the ring opening is carried out under conditions of elevated pressure.

The ring opening reaction can be represented thus:

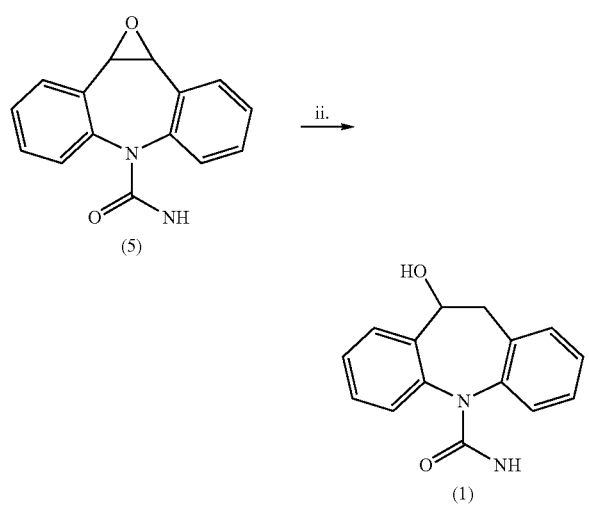

Advantageously, the ring-opening of the epoxide (5) is carried out by catalytic hydrogenation with gaseous hydrogen at elevated pressure, in the presence of a catalyst. As mentioned above, we have found that by using elevated pressure, it is possible to obtain good yields and purity, on an industrial scale, and we have been able to reduce the level of solvent required in the reaction.

A suitable catalyst, typically a metal catalyst, may be added to a stirred solution of the epoxide (5) in a suitable solvent mixture, containing an optional organic base.

The preferred catalyst is palladium, preferably adsorbed on an inert support such as charcoal and normally 5-10 wt % palladium on the support is used. More preferably there is 5-7 wt % palladium on the support. It is preferred that the total amount of palladium catalyst is 0.001 to 0.01 mol % (based on the amount of the epoxide (5). A typical catalyst loading is 0.0015 mol % (0.013 wt %). We have found that the optimum selection of the catalyst improves the yield of the reaction.

Preferred solvents for the reaction include chlorinated alkanes, such as dichlorolmethane, alcohols having from 1 to 6 carbon atoms, such as methanol, ethanol or isopropanol, and water, or the reaction can be run in mixtures of the above mentioned solvents. We have obtained the best results with methanol and water. The addition of water improves the reaction by reducing side products. Preferably the methanol is present in an amount of up to about 20 volumes to one volume of the epoxide, with about 10 volumes of methanol to one volume of epoxide being preferred. The water is preferably present in an amount of up to about one volume to one volume of the epoxide, with about 0.3 volumes of water to one volume of epoxide being preferred.

The reaction can also be improved by the use of an organic base, especially trialkylamines, such as triethylamine. This speeds the reaction up, thus resulting in the formation of fewer side products and greater yield. We have found that the reaction works well with a small, catalytic quantity of the organic base, such as triethylamine. Preferably the amount of the organic base, on a molar basis, is less than the amount of the epoxide, and most preferably there is no more than 0.1 mol % organic base, based on the amount of the epoxide. Still more preferably there is from 0.03 mol % to 0.07 mol %, most preferably 0.05 mol %, of the organic base based on the amount of the epoxide.

Hydrogen gas may be bubbled through the reaction mixture, and, on completion of the reaction (after, e.g., 1-2 hours), the catalyst may be recovered by filtration and the product may be isolated as described below. The trialkylamine is preferably present in small quantities—preferably just enough is used to ensure that the reaction solution is alkaline.

The pressure may be from 200 kPa to 4.0 MPa. The pressure is preferably greater than or equal to 500 kPa, more preferably greater then or equal to 1.0 MPa. Preferably the pressure is 2.0 MPa or less, more preferably 1.5 MPa or less. In the preferred embodiment, the pressure is in the range 1.0 MPa to 2.0 MPa, with pressures from 1.0 MPa to 1.5 MPa being especially preferred. (All pressures stated in this application are absolute pressures, not gauge.)

It is preferred that the reaction is carried out at elevated temperature, i.e., above 25° C. More preferably, the reaction temperature is from 40° C. to 80° C. The reaction temperature is most preferably from 50° C. to 60° C., with temperatures from 50° C. to 55° C. being especially preferred. In practice, there is generally little need to carry out the reaction at temperatures above about 65° C., as no improvements were noted above this temperate.

After the reaction is complete (which typically takes 1-2 hours), the catalyst may be recovered by filtration through celite or silica, and the filtrate may be evaporated under vacuum. If desired, the crude product may be recrystallised from a suitable solvent such as ethyl acetate or lower alcohols such as ethanol.

Yields in both the catalytic hydrogen transfer and the catalytic hydrogenation reactions are usually from 85-90% and product purity is usually greater than 98%.

One particularly preferred specific process is as follows. The epoxide (5) is first slurried in methanol and a trace of triethylamine is added. The suspension is charged into an autoclave, and a slurry of palladium catalyst and water is added. For 70 minutes the mixture is hydrogenated at 55° C. and 1.5 MPa. The progress of the reaction is tested by HPLC, and when the level of epoxide is less than or equal to 1% a/a, the catalyst is removed by filtration. The filtrate is washed once with methanol. The combined product solution is then subjected to evaporation (at 70 kPa, 65° C.) and around 80% of the methanol is distilled off. Isopropanol is added and the rest of the methanol is distilled off. The resulting suspension is cooled to 0-5° C. to complete the precipitation of the compound (1). After cooling, the mixture is stirred for a further 2 hours at this temperature, then filtered. The filter cake is washed with a mixture of isopropanol and deionised water (the isopropanol and water in the mixture being present in a 1:1 ratio). Finally, the product is dried at 80° C. under vacuum for several hours.

The 11a,10b-dihydro-6H-dibenz/b,f/oxireno[d]azepine-6-carboxamide (5) is preferably formed by the epoxidation process described in WO02/96881. The major features of this process are set out below, and additional details may be found in W O02/96881.

The reaction described in WO02/96881 proceeds as follows:

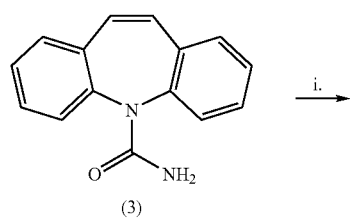

(3)

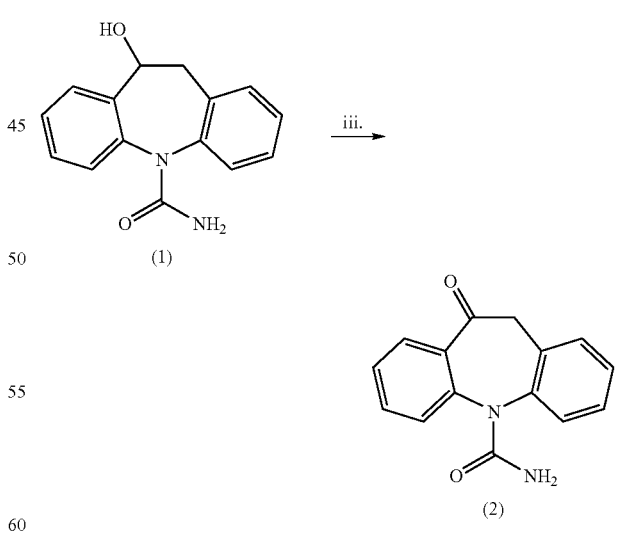

The epoxidation of carbamazepine is desirably carried out by addition of excess peroxyacetic acid to a stirred suspension of carbamazepine (3) and a metal catalyst in an inert solvent. The reaction may be carried out in the presence of an inorganic base. Peroxyacetic acid is cheap and readily available commercially as a solution in acetic acid or can be prepared in situ from mixtures of acetic acid and hydrogen peroxide (Hudlicky, M. Oxidations in Organic Chemistry, ACS Monograph, Washington D.C., 1990). Preferably 1.5-3 molar equivalents of peroxyacetic acid are used.

Suitable inert solvents include chlorinated hydrocarbons. The inorganic base may be, for example, sodium acetate, sodium carbonate or potassium carbonate, all of which are readily available and inexpensive; it is preferred that 2.5-3.2 molar equivalents of the inorganic base be used. Several metal catalysts are suitable for the epoxidation reaction including complexes of manganese, cobalt, nickel, copper, rhodium and iron.

The preferred catalysts are manganese (III) salen and potassium permanganate. Normally, 0.025-3 mol % of catalyst is desirable for good conversion. If preferred, a phase-transfer catalyst such as, for example Adogen 464 or Aliquat 336 may be used. If desired, the metal catalyst may be supported on an inert support such as alumina, silica or inert clay, in the form of powders, pellets or beads allowing for better recovery after reaction by simple filtration, an important factor due to environmental issues. Normally a 2-4% w/w supported catalyst is preferable.

Alternatively and if desired, the order of addition of the reagents may be reversed and carbamazepin-e (3) may be added to a solution of peroxyacetic acid and catalyst in the preferred solvent system. In either case, after the mildly exothermic reaction is complete, the inorganic base and supported metal catalyst may be removed by filtration and the filtrate may be stirred with aqueous sodium sulphite solution to destroy excess peroxide. The organic phase may then be separated, washed with water and sodium bicarbonate. The crude epoxide (5) may be obtained by evaporation of the organic solvent and can be purified, if desired, from a suitable solvent such as ethyl acetate or alcohols having from 1 to 6 carbon atoms, such as ethanol or isopropanol. The yield is usually above 85% and the product is usually >97% pure by HPLC analysis.

If desired, the 10,11-dihydro-10-hydroxy-5H-dibenz/b,f/azepine-5-carboxamide (1) formed by the process described above may be converted into a salt. It may also be resolved into a one or both of its R-(+)- and S-(−)-isomers. The salt may be foiled before or after the resolution step.

The 10,11-dihydro-10-hydroxy-5H-dibenz/b,f/azepine-5-carboxamide (1) may be used as an intermediate in the preparation of other important compounds.

For example, the 11a,10b-dihydro-6H-dibenz/b,f/oxireno [d]azepine-6-carboxamide (5) may be used to form oxcarbazepine by the process described in WO02/96881. The major features of this process are set out below, and additional details may be found in WO02/96881.

The reaction described in WO02/96881 proceeds as follows:

The oxidation of the alcohol (1) is carried out by addition of an excess of peroxyacetic acid to a stirred suspension of the alcohol (1) and a metal catalyst in a suitable solvent. If desired, a phase-transfer catalyst such as for example Adogen 464 or Aliquat 336 may be used. Usually 3-5 molar equivalents of peroxyacetic acid are required. Suitable solvents include chlorinated alkanes such as for example, dichloromethane or 1,2-dichloroethane. Preferred metal catalysts are chromium trioxide, manganese dioxide, manganese (III) acetate, potassium permanganate, cobalt (II) chloride and potassium and sodium dichromate. If desired, the metal catalyst may be supported on an inert support such as alumina, silica or inert clay, in the form of powders, pellets or beads allowing for better recovery after reaction by simple filtration. Normally a 2-4% w/w supported catalyst is preferable and typically 0.5-5 mol % of the metal catalyst is used for the oxidation reaction.

Alternatively and if desired, the order of addition of the reagents may be reversed and the solid alcohol (1) may be added to a solution of peroxyacetic acid and catalyst in the preferred solvent system. After the mildly exothermic reaction is complete, the supported metal catalyst may be removed by filtration and the filtrate may be stirred with aqueous sodium sulphite solution to destroy excess peroxide. The organic phase may then be separated, washed with water and sodium bicarbonate. The crude oxcarbazepine (2) may be obtained by evaporation of the organic solvent and can be purified if preferred from a suitable solvent such as ethyl acetate or alcohols having 1 to 6 carbon atoms such as for example, ethanol or isopropanol. The yield is usually above 85% and the product is usually >97% pure.

According to another aspect of the invention there is provided a method for the preparation of a compound of the formula (6):

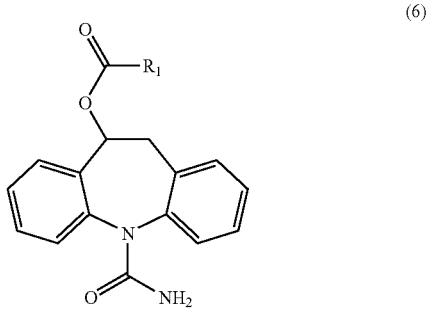

(6)

where $R_1$ is hydrogen, allyl, halogenalkyl, aralkyl, cycloalkyl, cycloalkylalkyl, alkoxy, aryl, or pyridyl; the term allyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming 10,11-dihydro-10-hydroxy-5H-dibenz/b,f/azepine-5-carboxamide (1) by a method as described above, then treating the 10,11-dihydro-10-hydroxy-5H-dibenz/b,f/azepine-5-carboxamide (1) to produce the compound of formula (6). The compound of formula (6) is preferably prepared by acylating the 10,11-dihydro-10-hydroxy-5H-dibenz/b,f/azepine-5-carboxamide (1).

The compound of formula (6) is described in more detail in our U.S. Pat. No. 5,753,646, the contents of which are incorporated herein by reference. The method can be used to produce any of the compounds disclosed in U.S. Pat. No. 5,753,646. For example, to produce 10-acetoxy-10,11-dihydro-5H-dibenz/b,f/azepine-5-carboxamide it is possible to add acetylchloride in dichloromethane to a suspension of 10,11-dihydro-10-hydroxy-5H-dibenz/b,f/azepine-5-carboxamide and pyridine in dichloromethane, as described in example 4, of U.S. Pat. No. 5,753,646.

The compounds described in examples 4 to 17 of U.S. Pat. No. 5,753,646 can be produced by acylation using the appropriate acyl halide. The compounds described in examples 18 to 23 can be produced using the appropriate carboxylic acid.

Using the present invention it is therefore possible to produce the following compounds:
1. 10-acetoxy
2. 10-benzoyloxy-10,11-dihydro-5H-dibenz/b,f/azepine-5-carboxamide
3. 10-(4-methoxybenzoyloxy)-10,11-dihydro-5H-dibenz/b,f/azepine-5-carboxamide
4. 10-(3-methoxybenzoyloxy)-10,11-dihydro-5H-dibenz/b,f/azepine-5-carboxamide
5. 10-(2-methoxybenzoloxy)-10,11-dihydro-5H-dibenz/b,f/azepine-5-carboxamide
6. 10-(4-nitrobenzoyloxy)-10,11-dihydro-5H-dibenz/b,f/azepine-5-carboxamide
7. 10-(3-nitrobenzoyloxy)-10,11-dihydro-5H-dibenz/b,f/azepine-5-carboxamide
8. 10-(2-nitrobenzoyloxy)-10,11-dihydro-5H-dibenz/b,f/azepine-5-carboxamide
9. 10-(4-chlorobenzoyloxy)-10,11-dihydro-5H-dibenz/b,f/azepine-5-carboxamide
10. 10-(3-chlorobenzoyloxy)-10,11-dihydro-5H-dibenz/b,f/azepine-5-carboxamide
11. 10-(2-acetoxybenzoyloxy)-10,11-dihydro-5H-dibenz/b,f/azepine-5-carboxamide
12. 10-propionyloxy-10,11-dihydro-5H-dibenz/b,f/azepine-5-carboxamide
13. 10-butyryloxy-10,11-dihydro-5H-dibenz/b,f/azepine-5-carboxamide
14. 10-pivaloyloxy-10,11-dihydro-5H-dibenz/b,f/azepine-5-carboxamide
15. 10-[(2-propyl)penatanoyloxy]-10,11-dihydro-5H-dibenz/b,f/azepine-5-carboxamide
16. 10-[(2-ethyl)hexanoyloxy]-10,11-dihydro-5H-dibenz/b,f/azepine-5-carboxamide
17. 10-stearoyloxy-10,11-dihydro-5H-dibenz/b,f/azepine-5-carboxamide
18. 10-cyclopentanoyloxy-10,11-dihydro-5H-dibenz/b,f/azepine-5-carboxamide
19. 10-cyclohexanoyloxy-10,11-dihydro-5H-dibenz/b,f/azepine-5-carboxamide
20. 10-phenylacetoxy-10,11-dihydro-5H-bibenz/b,f/azepine-5-carboxamide
21. 10-(4-methoxyphenyl)acetoxy-10,11-dihydro-5H-dibenz/b,f/-azepine-5-carboxamide
22. 10-(3-methoxyphenyl)acetoxy-10,11-dihydro-5H-dibenz/b,f/azepine-5-carboxamide
23. 10-(4-nitrophenyl)acetoxy-10,11-dihydro-5H-dibenz/b,f/azepine-5-carboxamide
24. 10-(3-nitrophenyl)acetoxy-10,11-dihydro-5H-dibenz/b,f/azepine-5-carboxamide
25. 10-nicotinoyloxy-10,11-dihydro-5H-dibenz/b,f/azepine-5-carboxamide
26. 10-isonicotinoyloxy-10,11-dihydro-5H-dibenz/b,f/azepine-5-carboxamide
27. 10-chloroacetoxy-10,11-dihydro-5H-dibenz/b,f/azepine-5-carboxamide
28. 10-bromoacetoxy-10,11-dihydro-5H-dibenz/b,f/azepine-5-carboxamide
29. 10-formyloxy-10,11-dihydro-5H-dibenz/b,f/azepine-5-carboxamide 30. 10-ethoxycarbonyloxy-10,11-dihydro-5H-dibenz/b,f/azepine-5-carboxamide
31. 10-ethoxycarbonyloxy-10,11-dihydro-5H-dibenz/b,f/azepine-5-carboxamide As mentioned above, the 10,11-dihydro-10-hydroxy-5H-dibenz/b,f/azepine-5-carboxamide may be resolved into its (R)-(+)- and (S)-(−)-stereoisomers, whereby the desired (R)-(+)- or (S)-(−)-stereoisomer of the above compounds (1) to (31) may be produced.

These compounds, or pharmaceutically acceptably derivatives thereof (such as s alts), can be used in the preparation of pharmaceutical compositions comprising the compound itself, or the derivative, in combination with a pharmaceutically acceptable carrier. Such compositions have anticonvulsant properties and can be used in the treatment of some central and peripheral nervous system disorders, such as epilepsy.

The invention disclosed herein will be exemplified by the following examples of preparation, which should not be construed to limit the scope of the disclosure. It is to be understood that the invention is not to be limited to the exact details of operation as obvious modifications and equivalents will be apparent to those skilled in the art.

EXAMPLE 1

11a,10b-Dihydro-6H-dibenz/b,f/oxireno[d]azepine-6-carboxamide (5)

To a stirred suspension of carbamazepine (3) (200 g, 847.5 mmol) and sodium carbonate (287.4 g, 2711 mmol) in dichloromethane (1000 ml) were added tablets of potassium permanganate supported on alumina (3.5% w/w, 3.46 g, 0.771 mmol). Thereafter, peroxyacetic acid (39% solution in acetic acid, 432 ml, 2538 mmol) was added dropwise over one hour, causing a gradual rise in temperature until gentle reflux of the solvent. The mixture was stirred for twenty minutes and then allowed to stand for twenty minutes. The sodium carbonate and supported catalyst were then removed by filtration and washed by dichloromethane (200 ml); the alumina beads were separated from sodium carbonate by screening through a sieve. The combined filtrate was then stirred with an aqueous solution of sodium sulphite (20 g) and sodium bicarbonate (20 g) in water (250 ml) for one hour. The phases were then separated and the aqueous phase extracted by dichloromethane (50 ml). The combined organic layers were washed by water (100 ml), saturated aqueous sodium bicarbonate (100 ml), water again (100 ml) and brine, then dried over anhydrous sodium sulphate and filtered. Evaporation of the solvent (rotary evaporator, water aspirator pressure, 40° C.) gave the crude epoxide (5) as a beige solid which was crystallised from ethyl acetate (100 ml) to give the product as an off-white solid, 194.2 g, (91% yield).

EXAMPLE 2

10,11-Dihydro-10-hydroxy-5H-dibenz/b,f/azepin-5-carboxamide (1)

To 105 g water wet epoxide (i.e. 69.5 g dry) 600 ml methanol and 1.9 ml triethylamine were added. The slurry was stirred for 10 min at 20-30° C. and then transferred into a 1000 ml stainless steel autoclave and rinsed with 100 ml methanol. A slurry of 0.89 g palladium on charcoal (50% water wet) in 10 ml water was added. It was rinsed with 10 ml water. After inertisation with nitrogen (3×) the autoclave was flushed with hydrogen (2×). The hydrogenation was performed at 10-15 bar $H_2$ pressure and 50-55° C. (1000 rpm, reaction time ca. 70 min.) After complete hydrogen consumption, the reaction mixture was stirred for further 30 min. to ensure complete conversion. The conversion was checked by an in process test (HPLC: epoxide<=1.0% a/a). The catalyst was removed by filtration and the filtrate was washed with 80 ml methanol. The filtrate was concentrated in vacuo (70-75 kPa, 51-61° C. temperature of the distillate) from about 900 ml to 180-190 ml. The residue was cooled to about 40-45° C. and 200 ml isopropanol was added. The distillation was repeated (100 kPA, 70-80° C., ca. 145 ml distillate) to remove the methanol completely. The residue was cooled to 0-5° C. and was stirred at this temperature for at least 2 hours for crystallisation. The precipitate was filtered and washed with 80 ml isopropanol/water (1:1). The wet product (ca. 68 g) was dried in vacuo to yield 58.8 g racemic alcohol. [Yield 82%]

It will be appreciated that the invention described above may be modified.

The invention claimed is:

1. A process for the preparation of 10,11-dihydro-10-hydroxy-5H-dibenz/b,f/azepine-5-carboxamide (1) by ring opening of 11a,10b-dihydro-6H-dibenz/b,f/oxireno[d]azepine-6-carboxamide (5), characterised in that the ring opening is carried out under conditions of elevated pressure.

2. The process according to claim 1, wherein the ring opening is performed by catalytic hydrogenation with gaseous hydrogen at elevated pressure in the presence of a catalyst.

3. The process according to claim 1, wherein the pressure is from 200 kPa to 4.0 MPa.

4. The process according to claim 1, wherein the pressure is from 1.0 MPa to 1.5 MPa.

5. The process according to claim 1, wherein the reaction is carried out at a temperature from 40° C. to 65° C.

6. The process according to claim 1, wherein the reaction is carried out at a temperature from 50° C. to 60° C.

7. The process according to claim 1, wherein the ring-opening reaction is carried out in the presence of a metal catalyst.

8. The process according to claim 7, wherein the metal catalyst used in the ring-opening reaction is 0.001-0.01 mol % palladium, based on the amount of the 11a,10b-dihydro-6H-dibenz/b,f/oxireno[d]azepine-6-carboxamide (5).

9. The process according to claim 1, wherein the ring-opening reaction is carried out in the presence of an organic base which is a trialkylamine.

10. The process according to claim 1, wherein the ring-opening reaction is carried out in a solvent selected from chlorinated hydrocarbons, alcohols having from 1 to 6 carbon atoms and water, or mixtures thereof.

11. The process according to claim 1, wherein the ring opening reaction is carried out in the presence of methanol, water and triethylamine.

12. A process for the preparation of 10,11-dihydro-10-oxo-5H-dibenz/b,f/azepine-5-carboxamide (2) comprising preparing 10,11-dihydro-10-hydroxy-5H-dibenz/b,f/azepine-5-carboxamide (1) by the process according to claim 1, then oxidising 10,11-dihydro-10-hydroxy-5H-dibenz/b,f/azepine-5-carboxamide (1) by reaction with peroxyacetic acid in the presence of a metal catalyst in a substantially inert solvent.

13. A process for the preparation of a compound of the formula (6):

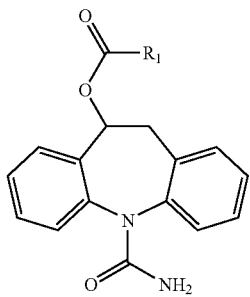 (6)

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming 10,11-dihydro-10-hydroxy-5H-dibenz/b,f/azepine-5-carboxamide (1) by the process according to claim 1, then treating the 10,11-dihydro-10-hydroxy-5H-dibenz/b,f/azepine-5-carboxamide (1) to produce the compound of formula (6).

14. The process according to claim 13, wherein the compound of formula (6) is prepared by acylating the 10,11-dihydro-10-hydroxy-5H-dibenz/b,f/azepine-5-carboxamide.

15. A process for the preparation of 10-acetoxy-10,11-dihydro-5H-dibenz/b,f/azepine-5-carboxamide comprising forming 10,11-dihydro-10-hydroxy-5H-dibenz/b,f/azepine-5-carboxamide by the process according to claim 1, then acylating the 10,11-dihydro-10-hydroxy-5H-dibenz/b,f/azepine-5-carboxamide with acetylchloride.

* * * * *